(12) United States Patent
Lee et al.

(10) Patent No.: US 6,399,591 B1
(45) Date of Patent: Jun. 4, 2002

(54) CHARGEABLE PHARMACEUTICAL TABLETS

(75) Inventors: Fang-Yu Lee; Fang-Chen Lee, both of Taichung (TW)

(73) Assignee: Yung-Shin Pharmaceutical Ind. Co., Ltd., Taipei (TW)

( * ) Notice: Subject to any disclaimer, the term of this patent is extended or adjusted under 35 U.S.C. 154(b) by 0 days.

(21) Appl. No.: 09/487,961

(22) Filed: Jan. 19, 2000

(51) Int. Cl.⁷ .............. A61K 31/695; A61K 9/20; A61K 47/00
(52) U.S. Cl. .............. 514/63; 424/464; 424/474; 427/240; 514/769; 514/772
(58) Field of Search ................... 424/451, 452, 424/463, 464, 457, 474, 493, 494, 489, 490; 514/63, 769, 772; 427/240; 118/52

(56) References Cited

U.S. PATENT DOCUMENTS

| | | | |
|---|---|---|---|
| 3,501,571 A | * 3/1970 | Kai-Ching Yen | 424/456 |
| 4,127,650 A | 11/1978 | Buehler | 424/184 |
| 4,198,390 A | * 4/1980 | Rider | 424/471 |
| 4,684,534 A | 8/1987 | Valentine | 427/3 |
| 5,073,384 A | 12/1991 | Valentine et al. | 424/474 |
| 5,558,880 A | * 9/1996 | Gole et al. | 424/484 |
| 5,660,860 A | * 8/1997 | Fielden | 424/464 |
| 5,731,339 A | * 3/1998 | Lowrey | 514/400 |

OTHER PUBLICATIONS

East online, file Derwent, Acc. No. 1974–42986V (SU 395121, "Coater, e.g. for pills—with an inside bath filled from an outside reservoir." (1973)), abstract.*
STN/CAS online, file CAPLUS, Acc. No. 1980:203591, Doc. No. 92:203591 (Sakauchi et al. JP 54154515 A2 (1979)), Abstract.*
STN/CAS online, fille EMBASE, Acc. No. 92039423, Doc. No. 1992039423 (Friis et al., Digestion (1991) 49/4 (227–230)), Abstract.*

* cited by examiner

Primary Examiner—Jose' G. Dees
Assistant Examiner—Frank Choi
(74) Attorney, Agent, or Firm—Fish & Richardson P.C.

(57) ABSTRACT

A blank tablet of this invention, typically, includes an absorbent, a disintegrant, a lubricant, and a diluent or a binder, or a mixture of a diluent and a binder. An active ingredient in liquid form is introduced into the blank tablet to produce a pharmaceutical composition.

4 Claims, No Drawings

CHARGEABLE PHARMACEUTICAL TABLETS

BACKGROUND

Pharmaceutical tablets are used to administer orally an active ingredient to a patient. In general, conventional pharmaceutical tablets are made by adding active ingredient(s) to a tablet in the granulation stage, in the granule finishing stage, or in the direct mixing stage. The final mixture is made into a tablet after being mixed homogeneously.

In general, orally administered pharmaceutical tablets have some disadvantages relative to orally administered active ingredients in liquid form. Typically, the rate at which the active ingredient acts on the patient is limited by the rate at which the pharmaceutical tablet dissolves.

SUMMARY

In general, a chargeable blank tablet of this invention contains no active ingredients. The active ingredients are introduced into the blank tablet, such as by immersing the blank tablet into the active ingredient in liquid form so that the blank tablet absorbs the active ingredients in liquid form. Whenever required, any excessive amount of the active ingredients in liquid form can be removed by centrifuging the tablets. The blank tablet including active ingredients in liquid form unexpectedly exhibits better potency than conventional pharmaceutical tablets containing the same active ingredient. In particular, pharmaceutical compositions produced with blank tablets of this invention unexpectedly exhibit fast release rates of the active ingredients absorbed into the tablet, e.g., the disintegration time of the tablet is quick relative to other conventional pharmaceutical tablets. In a specific example, a blank tablet including an anti-foaming active ingredient unexpectedly exhibits superior anti-foaming properties relative to conventional pharmaceutical tablets.

In one aspect, the invention features a blank tablet including between about 0.1 to about 5 weight percent of an absorbent; between about 10 to about 98 weight percent of a diluent or a binder; between about 0.5 to about 10 weight percent of a disintegrant; and between about 0.5 to about 5 weight percent of a lubricant. The blank tablet is formed to absorb an active ingredient in liquid form.

In another aspect, the invention features a method for preparing a pharmaceutical composition. The method includes forming a blank tablet and introducing an active ingredient in liquid form into the blank tablet. If necessary, the charged tablet can be centrifuged to remove any excessive amount of the active ingredient introduced into the blank tablet. The amount of the active ingredient, e.g., dimethylpolysiloxane and simethicone, introduced into the blank tablet is, typically, between about 1 to about 25 weight percent.

In a further aspect, the invention features pharmaceutical compositions produced by the method.

The details of one or more embodiments of the invention are set forth in the accompanying description below. Other features, objects, and advantages of the invention will be apparent from the description and from the claims.

DETAILED DESCRIPTION

A blank tablet of this invention, typically, includes the following components: an absorbent, a disintegrant, a lubricant, and a diluent or a binder (e.g., a mixture of a diluent and a binder). The components of the blank tablet can include any conventionally known absorbents, disintegrants, lubricants, diluents, and binders.

In general, a blank tablet of this invention includes between about 0.1 to about 5 weight percent, preferably between about 0.1 to about 2 weight percent, of the absorbent; between about 0.5 to about 5 weight percent, preferably between about 0.1 to about 2 weight percent, of the lubricant; between about 0.5 to about 10 weight percent, preferably between about 0.5 to about 5 weight percent, of the disintegrant; and between about 10 to about 98 weight percent, preferably between about 50 to about 95 weight percent, of a diluent or a binder.

An example of an absorbent includes but is not limited to silicon dioxide (i.e., silicon dioxide or a mixture of silicon dioxide and another absorbent). Examples of the lubricant include but are not limited to talc powder, stearate, or magnesium stearate. Possible disintegrants include but are not limited to sodium starch glycolate, sodium carboxymethyl cellulose, or calcium carboxymethyl cellulose. Examples of the diluent include but are not limited to monosacharides and disaccharides, e.g., glucose, mannitol, galactose, sorbitol, fructose, sucrose, and lactose. Possible binders include but are not limited to microcrystalline cellulose or directly compressed lactose.

The method of preparing a blank tablet of this invention includes sifting the absorbent, disintegrant, binder or diluent through a screen to remove large particulates. Typically, the absorbent, disintegrant, binder or diluent are passed through a 30 mesh screen prior to mixing, and the screened components are then combined with the lubricant and mixed or blended in a mixer. The blended mixture can be formed into tablets by a Fette high-speed tablet press. In general, the tablets have round shape with a diameter of about 9 mm and a thickness of between about 4.85 to about 5.15 mm.

The active ingredient in liquid form can be added to the blank tablet by any known method. For example, the blank tablet can be immersed in the active ingredient in liquid form. Alternatively, the active ingredient in liquid form can be sprayed, poured, or dropped (e.g., pipetted) onto the blank tablet. Once the blank tablets have been formed, an active ingredient in liquid form can be immediately added to the blank tablet to produce a pharmaceutical composition. Alternatively, the blank tablets can be stored, removed, and then converted into a pharmaceutical composition at a later time. For example, blank tablets produced at one location can be shipped to a different location that produces the active ingredient. In general, the pharmaceutical composition includes between about 1 to about 40 weight percent, preferably between about 1 to about 25 weight percent, of the active ingredient in liquid form. The exact amount of active ingredient in liquid form added to the blank tablet is controllable by centrifugation. For example, a blank tablet is weighed, immersed in the active ingredient in liquid form, removed, and reweighed. If the tablet has absorbed too much active ingredient in liquid form, the tablet is centrifuged to remove excess active ingredient in liquid form, and then reweighed. The process of centrifuging and weighing can be repeated until the tablet contains the desired amount of active ingredient in liquid form. Of course, if the tablet contains too little active ingredient in liquid form the tablet is either disregarded or re-immersed in the active ingredient in liquid form.

Examples of active ingredients in liquid form include but are not limited to liquids, such as dimethylpolysiloxane, simethicone, or mixtures thereof. Dimethylpolysiloxane and simethicone have antifoaming properties, i.e., they reduce the surface tension, and are used on patients suffering from excessive fullness in the abdomen or intestinal tympanites. Additionally, dimethylpolysiloxane and simethicone are used as an antifoaming agent prior to performing gastroscopic procedures. In some embodiments, the active ingredient can be a solid dissolved in a solvent to produce an active ingredient in liquid form. The solvent can be any solvent that does not dissolve the blank tablet but in which the active ingredient is soluble. Of course, more than one solid active ingredient can be dissolved in a suitable solvent to form active ingredients in liquid form. Additionally, a solid and a liquid active ingredient can be mixed together to form active ingredients in liquid form. If necessary, the mixture of the solid and the liquid active ingredients can include a solvent to dissolve the solid active ingredient.

Without further elaboration, it is believed that the above description has adequately enabled the present invention. The following specific examples are, therefore, to be construed as merely illustrative, and not limitative of the remainder of the disclosure in any way whatsoever. All of the publications cited herein, including patents, are hereby incorporated by reference in their entirety.

A blank tablet of this invention was used to produce five pharmaceutical compositions including an anti-foaming active ingredient, i.e., dimethylpolysiloxane or simethicone. The pharmaceutical compositions can be used in eliminating bubbles in the gastric mucosa prior to gastroscopic surgery. The embodiments disclosed hereinafter are for examples only, and not for limiting the scope of the present invention.

| Pharmaceutical Composition 1 | |
|---|---|
| Tablet composition: | |
| Active ingredients: Dimethylpolysiloxane | 40 mg |
| Blank tablet: | |
| Silicon dioxide | 4 mg |
| Mix microcrystalline cellulose | 304 mg |
| Sodium starch Glycolate | 8 mg |
| Talc | 4 mg |
| Total | 360 mg |

The above composition was prepared as follows. Microcrystalline cellulose, sodium starch glycolate, and silicon dioxide were passed through a screen having a 30 mesh size. The screened materials and the talc were added to a mixer and blended for five minutes. The blended mixture was formed into blank tablets by a high speed tablet press.

The pharmaceutical composition was produced by immersing the blank tablet into dimethylpolysiloxane until the blank tablet absorbed the dimethylpolysiloxane to the specified amount, i.e., 40 mg. Whenever required, any excess active ingredient was removed by centrifugation.

| Pharmaceutical Composition 2 | |
|---|---|
| Tablet composition: | |
| Active ingredients: Simethicone | 50 mg |
| Blank tablet: | |
| Silicon dioxide | 4 mg |

| Pharmaceutical Composition 2 | |
|---|---|
| Lactose | 294 mg |
| Sodium glycolate starch | 8 mg |
| Magnesium stearate | 4 mg |
| Total | 360 mg |

The above composition was prepared as follows. Lactose, sodium starch glycolate, and silicon dioxide were mixed and passed through a screen having a 30 mesh size. The screened material and the magnesium stearate were added to a mixer and blended for five minutes. The blended mixture was formed into blank tablets by a high speed tablet press.

The pharmaceutical composition was produced by immersing the blank tablet into simethicone until the blank tablet absorbed the simethicone to the specified amount, i.e., 50 mg. Whenever required, any excess active ingredient was removed by centrifugation and then made into a tablet (blank tablet) by a tablet presses.

| Pharmaceutical Composition 3 | |
|---|---|
| Tablet composition: | |
| Active ingredients: Dimethylpolysiloxane | 80 mg |
| Blank Tablet: | |
| Silicon dioxide | 8 mg |
| Microcrystalline cellulose | 244 mg |
| Glucose | 244 mg |
| Calcium Carboxymethyl cellulose | 16 mg |
| Magnesium stearate | 8 mg |
| Total | 600 mg |

The above composition was prepared as follows. Microcrystalline cellulose, glucose, calcium carboxymethyl cellulose, and silicon dioxide were mixed and passed through a screen having a 30 mesh size. The screened materials and magnesium stearate were added to a mixer and blended for five minutes. The blended mixture was formed into blank tablets by a high speed tablet press.

The pharmaceutical composition was produced by immersing the blank tablet into dimethylpolysiloxane until the blank tablet absorbed the dimethylpolysiloxane to the specified amount, i.e., 80 mg. Whenever required, any excess active ingredient was removed by centrifugation.

| Pharmaceutical Composition 4 | |
|---|---|
| Tablet composition: | |
| Active ingredients: Dimethylpolysiloxane | 80 mg |
| Blank tablet: | |
| Silicon dioxide | 8 mg |
| Microcrystalline cellulose | 390.4 mg |
| Glucose | 97.6 mg |
| Sodium carboxymethyl cellulose | 16 mg |
| Magnesium stearate | 8 mg |
| Total | 600 mg |

The above composition was prepared as follows. Microcrystalline cellulose, glucose, sodium carboxymethyl cellulose, and silicon dioxide were mixed and passed through a screen having a 30 mesh size. The screened materials and magnesium stearate were added to a mixer and blended for five minutes. The blended mixture was formed into blank tablets by a high speed tablet press.

The pharmaceutical composition was produced by immersing the blank tablet into dimethylpolysiloxane until the blank tablet absorbed the dimethylpolysiloxane to the specified amount, i.e., 80 mg. Whenever required, any excess active ingredient was removed by centrifugation.

| Pharmaceutical Composition 5 | |
|---|---|
| Tablet composition: | |
| Active ingredients: Dimethylpolysiloxane | 80 mg |
| Blank tablet: | |
| Silicon dioxide | 8 mg |
| Microcrystalline cellulose | 97.6 mg |
| Glucose | 390.4 mg |
| Calcium carboxymethyl cellulose | 16 mg |
| Magnesium stearate | 8 mg |
| Total | 600 mg |

The above composition was prepared as follows. Microcrystalline cellulose, glucose, calcium carboxymethyl cellulose, and silicon dioxide were mixed and passed through a screen having a 30 mesh size. The screened materials and magnesium stearate were added to a mixer and blended for five minutes. The blended mixture was formed into blank tablets by a high-speed tablet press.

The pharmaceutical composition was produced by immersing the blank tablet into dimethylpolysiloxane until the blank tablet absorbed the dimethylpolysiloxane to the specified amount, i.e., 80 mg. Whenever required, any excess active ingredient was removed by centrifugation.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A pharmaceutical composition produced by a method comprising:

forming a blank tablet comprising between about 0.1 to about 5 weight percent of an absorbent, between about 10 to about 98 weight percent of a diluent or a binder, between about 0.5 to about 10 weight percent of a disintegrant, and between about 0.5 to about 5 weight percent of a lubricant;

introducing an active ingredient in liquid form into the blank tablet; and centrifuging the tablet to remove an excessive amount of the active ingredient introduced into the blank tablet.

2. A method for preparing a pharmaceutical composition, the method comprising:

forming a blank tablet comprising between about 0.1 to about 2 weight percent of an absorbent, between about 50 to about 95 weight percent of a diluent or a binder, between about 0.5 to about 5 weight percent of a disintegrant, and between about 0.1 to about 2 weight percent of a lubricant;

introducing an active ingredient in liquid form into the blank tablet; and centrifuging the tablet to remove an excessive amount of the active ingredient introduced into the blank tablet.

3. The method of claim 2, wherein the active ingredient is dimethylpolysiloxane or simethicone.

4. A pharmaceutical composition produced by the method of claim 3.

* * * * *